United States Patent [19]

Collins

[11] 4,219,545
[45] Aug. 26, 1980

[54] TREATMENT OF INFECTIOUS KERATOCONJUNCTIVITIS IN ANIMALS

[76] Inventor: Calvin E. Collins, Mendon, Mo. 64660

[21] Appl. No.: 23,304

[22] Filed: Mar. 23, 1979

[51] Int. Cl.² .................. A61K 31/65; A61K 31/71; A61K 31/525

[52] U.S. Cl. .................. 424/181; 424/227; 424/252

[58] Field of Search .................. 424/252, 181, 227

[56] References Cited

U.S. PATENT DOCUMENTS

| 2,388,261 | 11/1945 | Front . | |
| 3,754,084 | 8/1973 | Fujie et al. | 424/181 |

FOREIGN PATENT DOCUMENTS

| 131038 | 1/1949 | Australia | 424/252 |
| 2147894 | 4/1972 | Fed. Rep. of Germany | 424/252 |

OTHER PUBLICATIONS

Chem. Abst. 67 47089(j) (1967)–Saikovs'ka et al.
Chem. Abst. 80 55814(a) (1974)–Lipkan et al.
Chem. Abst. 81 86059(h) (1974)–Lipkan et al.

Primary Examiner—Douglas W. Robinson
Attorney, Agent, or Firm—Fishburn, Gold and Litman

[57] ABSTRACT

The oral administration to animals of riboflavin is an effective therapeutic treatment for keratoconjunctivitis. Suitable riboflavin dosages for this treatment are in the nature of from about 65 milligrams to about 200 milligrams per animal per day. The riboflavin may be orally administered by mixing with ground feed or corn or by incorporation with mineral salt into a salt lick. Additional ingredients with the riboflavin such as antibiotics, vitamin A and other vitamins assist in the treatment. Suitable antibiotics include tetracycline, neomycin, and oxytetracycline.

7 Claims, No Drawings

TREATMENT OF INFECTIOUS KERATOCONJUNCTIVITIS IN ANIMALS

BACKGROUND OF THE INVENTION

The present invention relates to a method of treatment for eye infections in animals, in particular cattle.

Each year a great number of cattle are rendered partially or totally blind on a temporary or permanent basis due to the effects of keratoconjunctivitis, commonly known as "pink eye". An effective, simple and relatively inexpensive treatment for pink eye is thus desired to prevent the harmful results of the disease without producing unwanted side effects.

OBJECTS AND SUMMARY OF THE INVENTION

Therefore, the objects of the present invention are: to provide a treatment for infectious keratoconjunctivitis in animals, especially cattle; to provide such a method which is effective in reducing the symptoms of keratoconjunctivitis; to provide such a method which comprises the oral administration of riboflavin to so infected animals; to provide a composition of riboflavin and carriers which induce infected animals to partake thereof; to provide a composition of riboflavin and other ingredients such as antibiotics and vitamins to facilitate the heating process; and to provide such a method which is relatively inexpensive, simple to use and particularly well adapted for the proposed use thereof.

Other objects and advantages of this invention will become apparent from the following description wherein is set forth, by way of example, certain embodiments of this invention.

DETAILED DESCRIPTION OF PREFERRED EMBODIMENTS

As required, detailed embodiments of the present invention are disclosed herein, however, it is to be understood that the disclosed embodiments are examplary of the invention which may be embodied in various forms. Therefore, specific details disclosed herein are not to be interpreted as limiting, but merely as a basis for the claims and as a representative basis for teaching one skilled in the art to variously employ the present invention in virtually any appropriately detailed method.

A successful treatment for infections keratoconjunctivitis (also known as "pinkeye" and infections ophtalmia) in animals, especially cattle, has been found which comprises the oral ingestion of riboflavin (also known as vitamin $B_2$, lactoflavin, 6,7-dimethyl-9-d-ribitylisoalloxazine and active derivatives of vitamin $B_2$) in amounts substantially greater than the normal periodic requirement thereof in such an animal.

Inflamation of the conjunctiva and cornea of the eyes and an infective discharge from the eyes and nose are symptomatic of keratoconjunctivitis in cattle. In later stages of the disease the cattle often have their vision severly impaired or are totally blinded thereby. Oral administration to cattle having keratoconjunctivitis of preferably from about 65 milligrams to about 200 milligrams per animal per day of riboflavin has demonstrated marked physical improvement and in most cases apparent complete remission of the disease, as shown by the aveyance of the above noted symptoms. Although greater amounts than 200 milligrams per day per animal of riboflavin are not believed to be injurious to the animal, greater amounts than 200 milligrams were not found to improve the scope or speed of recovery from the disease over the preferred range. In addition, for purposes of prophylaxis or for treatment of a mildy diseased animal, amounts less than 65 milligrams per day per animal were found to be suitable. The most effective dosage of riboflavin for treatment of an average case of keratoconjunctivitis in cattle was found to be in the nature of 141 milligrams thereof per day per animal.

Oral administration to cattle having keratoconjunctivitis of vitamin A in conjunction with the riboflavin was found to improve the healing process. Preferred ranges of vitamin A were from about 0.25 parts to about 12 parts thereof to each one part of riboflavin by weight.

In addition, the oral administration to cattle of compatible antibiotics in conjunction with the riboflavin was also found to improve the healing process. Preferred ranges of antibiotics were found to be from about 0.2 parts to about 4 parts thereof to each one part of riboflavin by weight. Suitable antibiotics include tetracycline hydrochloride (also referred to as tetracycline and marketed under the brand name "Achromycin"), neomycin (marketed under the brand names "Mycifrodin" and "Neobiotic"), oxytetracycline dihydrate (also referred to as oxytetracycline and marketed under the brand name "Terramycin") and combinations thereof.

Administration of riboflavin compositions according to the present invention to a large heard of cattle individually by hand is difficult, if not impossible, therefore the animals are preferably induced to voluntarily partake of the ingredients of the present invention by mixing same with some food supply, the typical consumption of which is known. Particularly suitable carriers of such riboflavin compositions are corn, other various ground feeds, or mineral salt in the form of salt licks. The riboflavin compositions can be mixed with such carriers by conventional methods such as blending in a feed mixer or adding same to conventional salt lick formulations. When ground feed is used as a carrier, preferred admixtures have been found to be in the nature of about 1 part riboflavin to about 400 parts of ground feed by weight. When corn is used as a carrier the preferred admixture has been found to be in the nature of about 1 part riboflavin to about 120 parts corn by weight. When salt is used as the carrier the preferred admixture has been found to be from about 12.5 parts to about 25 parts of salt to each 1 part riboflavin by weight. These ratios are variable depending on the particular animal's normal daily intake of the carrier which is also dependent somewhat on the animal's breed, age and size, climate and/or other conditions.

It is foreseen that other vitamins and minerals in addition to those already discussed hereinabove may also be included in the riboflavin compositions according to this invention, in particular vitamins $B_1$ (thiamine) and $B_{12}$ (cyanotobalamin).

The examples which follow will serve to illustrate several riboflavin compositions and use thereof according to this invention:

EXAMPLES OF THE INVENTION

EXAMPLE I

A composition formed of the following ingredients (by weight):
  4 parts riboflavin
  1 part vitamin A 1 part tetracycline

EXAMPLE II

A composition formed of the following ingredients (by weight):
24 parts riboflavin
5 parts tetracycline

EXAMPLE III

The composition as in Example II to which is added:
282 parts vitamin A

EXAMPLE IV

A composition formed of the following ingredients (by weight):
1 part riboflavin
4 parts vitamin A
4 parts oxytetracycline

EXAMPLE V

A composition formed of the following ingredients and in the following ratio:

| | |
|---|---|
| 9.6 grams | Riboflavin |
| 4 grams | Oxytetracycline |
| 2.8 grams | Neomycin |
| 2.7 million U.S.P. XVI units | Vitamin A |
| 8 grams | Vitamin $B_1$ |
| 120,000 U.S.P. units | Vitamin $B_{12}$ |

The following are examples of treatment of keratoconjunctivitis in cattle using the compositions of the present invention.

EXAMPLE VI

Host animals having keratoconjunctivitis were orally administered an average of 141 milligrams of riboflavin per day per animal until healing was complete (healing was identified by a complete remission of the hereinabove described symptoms for keratoconjunctivitis).

EXAMPLE VII

Host animals having keratoconjunctivitis were fed ground feed with which had been thoroughly mixed riboflavin in a ratio of one ton of feed to 5 pounds of riboflavin until healing was complete.

EXAMPLE VIII

Host animals having keratoconjunctivitis which had been grazing on a relatively sparse range were fed ground feed with which had been thoroughly mixed the composition of Example V, such that 5 pounds riboflavin were present in the finished mixture for each one ton of feed. The extra ingredients of the present example, in comparison to Example VII, are believed to help restore natural health in range weakened animals, thereby helping such animals to absorb and facilitate the treatment of the present invention. The antibotics and vitamin A also appear to work in conjunction with the riboflavin and to speed abeyance of the disease.

EXAMPLE IX

Different groups of host animals each having keratoconjunctivitis were fed ground feed containing compositions as described in Examples I, II, III and IV respectively until healing was complete. The ratios of the feed to the compositions in each case were such that each animal received between 65 and 200 milligrams of riboflavin per day.

EXAMPLE X

Host animals having keratoconjunctivitis were fed corn having thoroughly mixed therewith one pound of the composition of Example II for each three hundred pounds of corn for a period of two days. Thereafter the animals were on a continuing basis provided with a demand salt lick having thoroughly mixed therein six pounds of the composition of Example I per fifty pounds of salt.

It is to be understood that while certain embodiments of this invention have been described herein, it is not to be limited to the specific compositions or examples herein described.

Having thus described the invention, what is claimed and desired to secure by Letters Patent is:

1. A method for treatment of cattle having keratoconjunctivitis comprising:
   (a) orally administering to each of said cattle a composition comprising riboflavin and an edible carrier, wherein the dosage of said riboflavin is greater than about 65 milligrams per 24 hour period.
2. The method according to claim 1 wherein:
   (a) said dosage is administered during consecutive 24 hour periods until symptoms of keratoconjunctivitis are no longer found in said cattle.
3. The method according to claim 1 wherein:
   (a) said dosage is about 141 milligrams per 24 hour period.
4. The method according to claim 1 wherein said composition also comprises per part by weight of riboflavin:
   (a) from about 0.2 to about 4 parts of compatible antibiotics; and
   (b) from about 0.25 to about 12 parts vitamin A.
5. The method according to claim 4 wherein:
   (a) said antibiotic is selected from the group consisting of tetracycline, neomycin, oxytetracycline, and combinations thereof.
6. The method according to claim 1 wherein:
   (a) said composition is mixed with feed for said cattle for purposes of administration in a range of about 120 parts to about 400 parts of said feed to each part of said riboflavin by weight.
7. The method according to claim 1 wherein:
   (a) said composition is mixed with edible salt for consumption by said cattle in a range of about 12.5 to about 25 parts of said salt to each part of said riboflavin by weight.

* * * * *